United States Patent [19]

Bänziger

[11] 4,452,242

[45] Jun. 5, 1984

[54] RESPIRATOR FOR USE IN PRESSURE CHAMBERS

[75] Inventor: Fritz Bänziger, Gross Wesenberg, Fed. Rep. of Germany

[73] Assignee: Drägerwerk Aktiengesellschaft, Fed. Rep. of Germany

[21] Appl. No.: 391,401

[22] Filed: Jun. 23, 1982

[30] Foreign Application Priority Data

Jul. 3, 1981 [DE] Fed. Rep. of Germany ....... 3126207

[51] Int. Cl.$^3$ ............................................ A61M 16/00
[52] U.S. Cl. .......................... 128/205.26; 128/200.24; 128/203.04; 137/624.14
[58] Field of Search ..................... 128/205.26, 204.24, 128/205.24; 137/624.14

[56] References Cited

U.S. PATENT DOCUMENTS

| | | | |
|---|---|---|---|
| 3,769,996 | 11/1973 | Holbrook et al. | 137/624.14 X |
| 3,916,889 | 11/1975 | Russell | 128/204.24 |
| 3,949,749 | 4/1976 | Stewart | 128/204.24 |
| 3,974,828 | 8/1976 | Bird | 137/624.14 X |
| 3,981,301 | 9/1976 | Warnow et al. | 128/204.24 |
| 4,007,736 | 2/1977 | Schreiber | 128/202.24 |
| 4,057,059 | 11/1977 | Reid et al. | 128/204.24 |
| 4,098,272 | 7/1978 | Stewart | 128/204.24 |
| 4,227,519 | 10/1980 | Warnow et al. | 128/205.24 |
| 4,227,523 | 10/1980 | Warnow et al. | 128/205.24 X |

FOREIGN PATENT DOCUMENTS 670305 6/1979 U.S.S.R. .......................... 128/205.26

Primary Examiner—Edward M. Coven
Attorney, Agent, or Firm—McGlew and Tuttle

[57] ABSTRACT

The respirator for use in pressure chambers serves to ventilate patients in therapeutic areas or in diver pressure chambers at diverse pressures. All its operations are effected pneumatically. The selected (a) ventilating volume supplied to the patient must remain constant (in operating liters) and the selected (b) breathing rate must be maintained. For meeting condition (a), the respirator contains a known pressure ratio regulator working on the double-diaphragm principle, and for meeting condition (b) it contains a frequency stabilizer. The frequency stabilizer contains in a housing a stepped piston moved by the chamber pressure against a spring, forming two volumes. The ratio of the free piston surfaces to each other determines the breathing time ratio. The volumes, adjusted by the chamber pressure over the height, determine the breathing rate together with the gas amount/time unit set by a precision adjusting valve. A varying chamber pressure for the controls has no effect on the breathing time ratio and the breathing rate. The respirator is equally suitable for use in therapeutic pressure chambers, like hyperbaric oxygen chambers, and for diver pressure chambers.

9 Claims, 3 Drawing Figures

RESPIRATOR FOR USE IN PRESSURE CHAMBERS

FIELD AND BACKGROUND OF THE INVENTION

This invention relates in general to respirators and in particular to a new and useful respirator for use in pressure chambers.

The use of pressure chambers for therapeutic purposes or the necessity of medical care in diver pressure chambers requires medical instruments and thus also respirators which can be used under pressure chamber conditions. The fully pneumatic respirators used here depend on the ambient pressure. The ventilation parameters set at atmospheric pressure, like respiratory output (AMV) and the breathing rate vary with the chamber pressure. During compression and decompression, constant readjustment is necessary.

A known respirator, particularly for infants, switches the inspiration and expiration phase by controlling the expiration valve from a time-control system composed of pneumatic parts. The pressure of the ventilating gas fed to the respirator through a filter, is reduced in a pressure reducer to the operating pressure. It serves to supply the patient and effects the operation of the time-control system. The ventilating air is fed to the patient over a flow valve and subsequently released into the atmosphere through an expiration valve controlled by the time-control system. The time-control system is composed of pneumatic logic elements which are connected in the form of two chains and are joined at their ends to form a bistable switch. Each chain determines the duration of a breathing phase to this end, a volume is provided in each chain which together with a precision regulating valve forms and RC-sector. After charging the respective volume to a switching pressure of 80% of the operating pressure, the other breathing phase is started by switching to the other chain, and at the same time the pressure is released in the charged volume.

Such a respirator is not suitable for use in pressure chambers. When the chamber pressure rises, the supply of ventilating gas is no longer sufficient. The flow valve must be constantly readjusted. Besides, higher chamber pressures cause a faster switching of the control for the breathing rate. Here, too, constant readjustment is necessary. (DE-OS No. 28 01 546).

SUMMARY OF THE INVENTION

The invention provides a respirator for use in pressure chambers, whose ventilation parameters, respirator output and breathing rate remain constant when the ambient pressure (chamber pressure) varies and where readjustments are not necessary.

In accordance with the invention there is provided a respirator for use in pressure chambers for supplying a respiration gas to a patient and which comprises a respiration line which is connected to the patient and which includes a control valve therein. Double diaphragm pressure ratio regulator is connected in the respiration line between the valve and the patient. This pressure ratio works on the double diaphragm principle and in addition there is provided a time control which controls a main valve for the ventilation gas current flow therethrough to the patient. The patient is connected through an expiration valve to atmosphere. The time control contains a frequency stabilizer which contains the housing with a stepped piston displaceable by the pressure chamber pressure against a spring and which discharges two distinct volumes to the ventilating gas current. The biasing force of the spring on the piston can be varied and the stroke of the piston can be controlled.

The use of (a) the pressure ratio regulator working on the double-diaphragm principle, ensures in a technically simple and proven manner a continuous exact supply to the patient of ventilating gas which is independent of the ambient pressure. The supply is effected with the set amount, that is, the amount in operating units remains always the same, independent of the ambient pressure.

The same holds true for the inspiration and expiration times relative to each other. The (b) frequency stabilizer with its simple mechanical construction, which is determined substantially by the stepped piston forming the two volumes, also ensure a constant breathing rate, even with varying ambient pressures.

The invention provides excellent results using (a) the pressure ratio regulator together with (b) the frequency stabilizer. The respirator is equally suitable for use in therapeutic pressure chambers, such as hyperbaric oxygen chambers, and for use in diver pressure chambers.

Accordingly it is an object of the invention to provide a respirator for use pressure chambers which includes a control of the inspiration and expiration phase by a time control using pneumatic controls wherein the time control controls a main valve for the ventilating gas flow to the patient which is followed by a pressure regulator and an expiration valve which is connected to the patient for discharging expiration air wherein the time control contains a frequency stabilizer which includes a slip piston displaceable in a comparable cylinder capable of discharging two separate volumes into the control line.

A further object of the invention is to provide a respirator which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
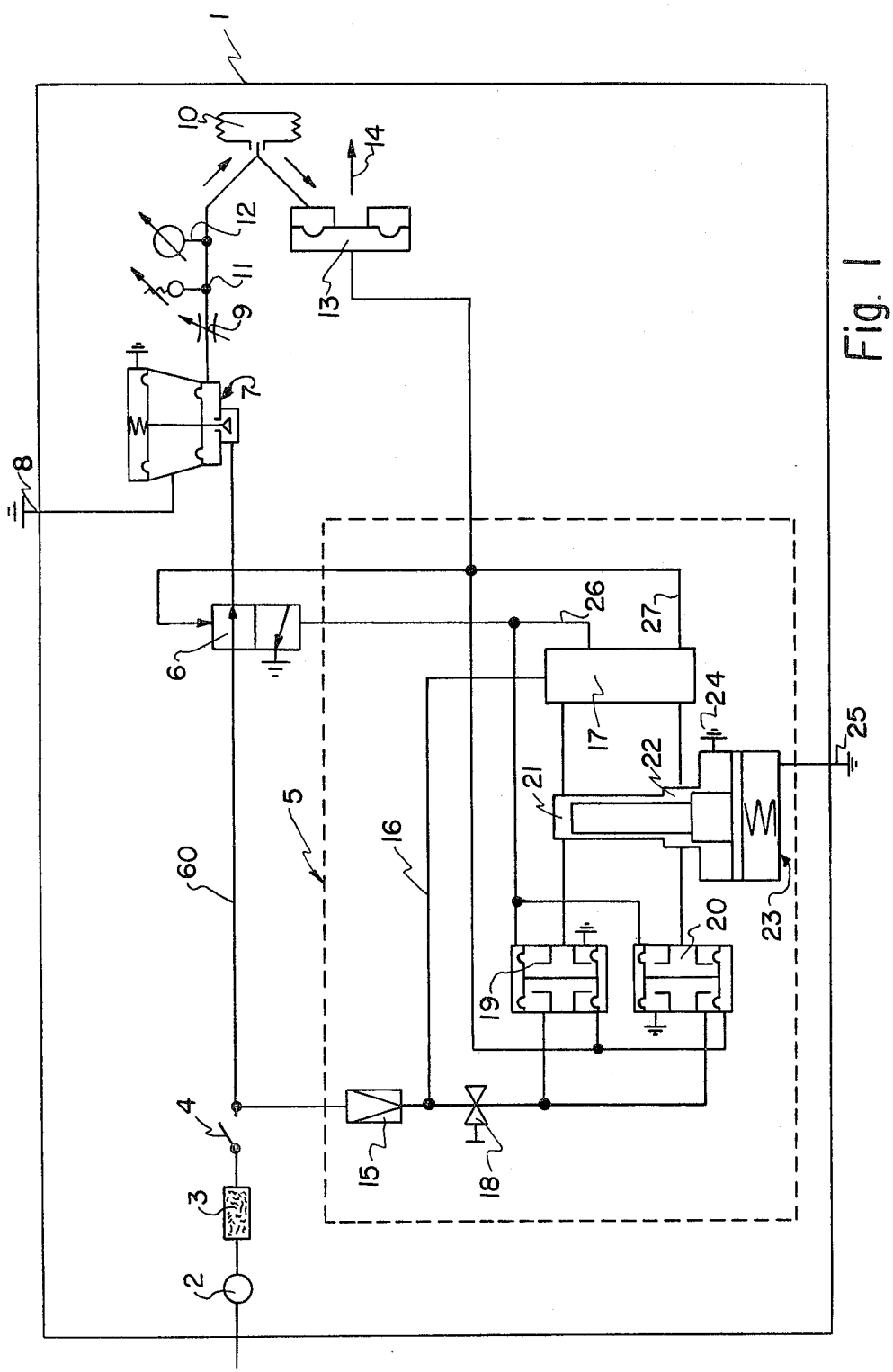
FIG. 1 is a diagrammatic representation of a respirator in a pressure chamber constructed in acccordance with the invention.

Referring to the drawings in particular the invention embodied therein comprises a respirator for use in a pressure chamber such as chamber 1 for supplying respiration gas to a patient which is indicated 10 and which comprises a respiration line 60 which is connected out to the exterior of the chamber 1 to a source of pressure gas through a connection 2. Double diaphragm pressure ratio regulator 7 is located in the respiration line 60 between the control valve 6 and the patient 10. In addition a time control 5 is connected to a terminal of a switch 4 for using the pressure gas for operations into the control valve 6 for regulating the flow in the respiration line 60.

Ventilating gas is fed to the respirator installed in pressure chamber 1 from a gas source arranged outside pressure chamber 1 at pressure gas connection 2. From there it flows through a filter 3 over a main switch 4 and main valve 6 operated by a time control generally designated 5. The gas passes through the valve 6 to pressure ratio regulator 7 and through a manually adjustable flow valve 9 to the patient represented symbolically by an elastic volume 10. A pressure limiter 11 and a pressure indicator 12 are connected to the ventilating gas line next to the patient. The expiration gas leaves the respirator at 14 over an expiration valve 13 operated by the time control 5 and it flows into the pressure chamber The time control 5 includes a pressure reducer 15 connected behind main switch 4 to the ventilating gas line. A flipflop 17 and two double-diaphragm valves 19, 20 are provided with ventilating gas as a propellant gas from the outlet of pressure reducer 15 over a line 16 and a precision adjusting valve 18 respectively. The double-diaphragm valves 19, 20 are connected each over a volume A at 21 and B at 22, arranged inside a frequency stabilizer 23, to the inputs of flipflop 17. The outputs 26, 27 of flipflop 17 control main valve 6 and expiration valve 13 and effect at the same time the switching of double-diaphragm valves 19, 20. This results in the following sequence of operations.

During the inspiration phase, output 27 of flipflop 17 is connected to line 16 and carries the necessary operating excess pressure for time control 5, that is, a 1-signal; output 26 carries the O-signal. Main valve 6 is thus open and expiration valve 13 is closed. Double diaphragm valve 20 is in closed position in which it releases the pressure in volume B 22 to the interior of the pressure chamber 1. Double diaphragm valve 19 is open and allows a gas current adjusted on precision adjusting valve 18 to enter volume A 21. Due to this charge, the pressure in volume A 21 rises. When it attains a switching pressure of 80% of the operating excess pressure, it causes the switching of flipflop 17 at its input, and thus a change of the breathing phase.

During the expiration phase, output 27 of flipflop 17 carries the O-signal and output 26 the 1-signal. Main valve 6 is thus open and expiration valve 13 is open. Double-diaphragm valve 19 is in closed position in which it releases the pressure in volume A 21 to the interior of the pressure chamber 1. Double diaphragm valve 20 is open and allows a gas current adjusted on precision adjusting valve 18 to enter volume B 22. Due to this charge, the pressure in volume A 21 rises. When it attains a switching pressure of 80% of the operating excess pressure, it causes the switching of flipflop 17 at its input, and thus a change of the breathing phase once more.

Figure 2:
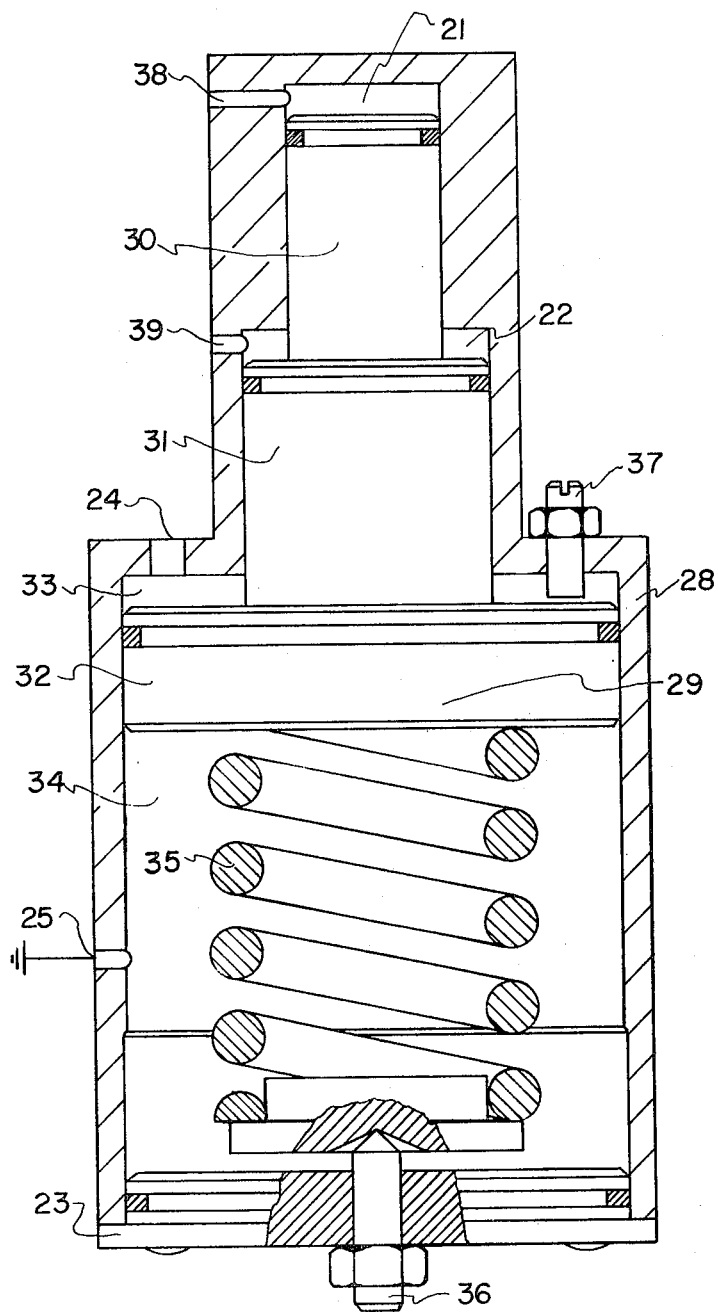
FIG. 2 is an enlarged somewhat schematic sectional view of a frequency stabilizer used with the time control shown in FIG. 1.

Frequency stabilizer 23 according to FIG. 2 contains a housing 28, a displaceable piston 29 with three stepped diameters. The upper piston part 30 encloses with its one end face opposite housing 28 volume A 21, the middle piston part 31 the annular volume B 22, and the bottom piston 32, chamber 33. Chamber 33 is connected over an opening 24 with the interior of chamber 1.

Underneath piston 29, housing 28 forms a closed spring chamber 34, which is connected over a connection 25 with the atmosphere outside pressure chamber 1. Between the end faces of spring chamber 34 and piston 29 is arranged a spring 35 whose force can be adjusted with an adjusting screw 36 in the end wall of spring chamber 34. An adjustable stop 37 in chamber 33 limits the stroke of piston 29. Volume A 21 is connected over opening 38 with flipflop 17 and double-diaphragm valve 19, volume B 22 over opening 39 with flipflop 17 and double-diaphragm valve 20. When the pressure in pressure chamber 1 corresponds to the pressure of the surrounding atmosphere, the large piston part 32 bears on stop 37, with spring 35 relaxed, and volume A 21 and B 22 have their minimum size. They are then alternatively filled up to a switching pressure.

The time required for filling up the respective volume determines the duration of the respective breathing phase. The given ratio of the cross-sectional area of the upper part 30 and of the annular surface of the middle piston part 31 determine the breathing time ratio, which does not vary, even in an axial displacement of piston 29.

The setting of precision adjusting valve 18 determines the time required for filling up volume A 21 and B 22, and thus always the ventilation rate.

To prevent a reduction of the filling time of volumes A 21 and B 22 with rising pressure in pressure chamber 1, while the setting of precision adjusting valve 18 remains unchanged, and an increase in the ventilation rate, the size of volumes A 21 and B 22 is correspondingly increased by displacing piston 29. This is effected by the axial pressure exerted in chamber 33 as well as in volumes A 21 and B 22 on piston 29 against the force of spring 35.

Figure 3:
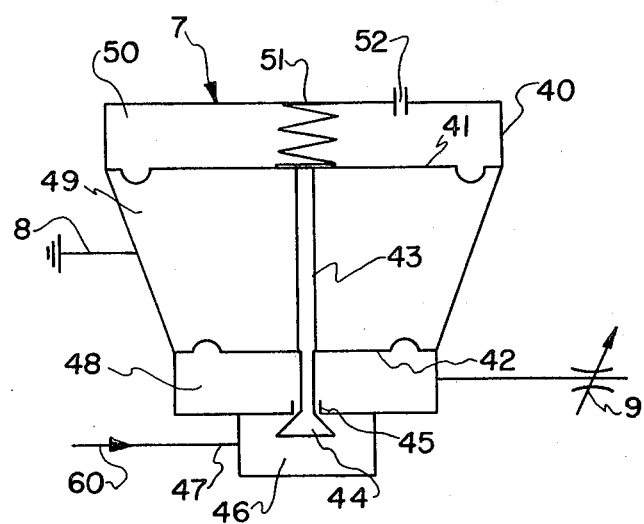
FIG. 3 is an enlarged sectional view of a pressure regulator shown in FIG. 1.

The pressure ratio regulator 7 according to FIG. 3 contains in a housing 40 a large diaphragm 41 and a small diaphragm 42. They are coupled with each other in the center by a bolt 43 and connected to a valve body 44 arranged outside the small diaphragm 42. Valve body 44 forms with its seat 45 a valve. The ventilating gas is fed in the direction of arrow 60 to a front pressure space 46 covering valve body 44 through a connection 47, a rear pressure space 48 between seat 45 and small diaphragm 42 is connected to flow valve 9. A space 49 between diaphragms 41, 42 is connected over connection 8 with the atmosphere outside pressure chamber 1. A spring chamber 50 arranged outside the large diaphragm 41 contains a compression spring 51 and is connected by an opening 52 with the pressure in pressure chamber 1. With the expiration gas supply closed, valve body 44 is lifted from seat 45.

Pressure ratio regulator 7 ensures a constant ventilation volume for the patient under any chamber pressure. He receives an amount of gas that is always the same in liters under any chamber pressure.

With rising chamber pressure in the chamber 1, the area differences between diaphragms 41, 42 causes valve 44, 45 to open and allows the ventilating air to enter under a higher pressure. The flow conditions vary proportionally to the pressure variation.

While specific embodiments of the invention have been shown and described in detail to illustrate the application of the principles of the invention, it will be understood that the invention may be embodied otherwise without departing from such principles.

What is claimed is:

1. A respirator for use in a pressure chamber having a pressure, for supplying a respiration gas to a patient during a breathing cycle having an inhalation time and an exhalation time, comprising:

a respiration line disposed in the pressure chamber for connection to a patient;

a control valve in said respiration line for passing an inhalation gas flow to the patient and for blocking gas flow on the respiration line;

a time control unit connected to said respiration line and to said control valve for controlling respiration gas during the inhalation and the exhalation times of the breathing cycle;

said time control unit including a frequency stabilizer comprising a cylinder having a plurality of cylinder portions of different diameters and a step piston having a plurality of portions in sliding sealing engagement with respective ones of said cylinder portions, said step piston portions defining with said cylinder portion said plurality of volumes, a first one of said volumes communicating with said pressure chamber for exposing a first one of said piston portions to the pressure of said pressure chamber, a second one of said volumes communicating with an exterior of said pressure chamber for exposing a second one of said piston portions to a pressure outside said pressure chamber, biasing means connected to said frequency stabilizer for biasing said piston in a selected direction in said cylinder for balancing a pressure outside said pressure chamber with the pressure inside said pressure chamber by displacement of said piston, a third and a fourth one of said volumes having a volume ratio corresponding to the ratio between said inhalation time and said exhalation time;

said time control unit further including control means connected between said third and fourth volumes, and said control valve for operating said control valve to pass an inhalation gas flow during the inhalation time and to block the gas flow during the exhalation time; and an exhalation valve for connection to the patient, connected to said control means for establishing an exhalation gas flow during the exhalation time.

2. A respirator according to claim 1, including cycle time adjustment means connected to said biasing means for adjusting a bias of said biasing means to adjust an overall respirator cycle time which equals inhalation time plus the exhalation time.

3. A respirator according to claim 1 including a double diaphragm pressure ratio regulator in said respiration line between said control valve and a portion of said respirator line adapted for connection to the patient.

4. A respirator according to claim 3 including stop means disposed in a path of movement of said piston for regulating the amount of movement of said piston relative to said cylinder.

5. A respirator according to claim 3, wherein said double diaphragm pressure regulator comprises a housing having two spaced-apart diaphragms of different diameters therein, defining in said housing a central chamber between said diaphragm and two end chambers, one on each side of said diaphragms facing away from said central chamber, said housing defining a pressure space exterior of one of said end chambers, with means defining a connection communicating said one of said end chambers with said pressure chamber, a valve body movably mounted to said housing for adjusting an opening of said connection, said pressure chamber connected to said respiration line and said one of said end chambers adapted for connection to the patient, one of said central chamber and the other of said end chambers communicating with an exterior of said pressure and the other of said central chamber and the other end chamber communicating with an interior of said pressure chamber for regulating a flow of respiration gas from said respiration line to the patient in accordance with a differential between pressurses on the exterior and the interior of said pressure chamber.

6. A respirator according to claim 1, wherein said control means includes a flipflip connected to said third and fourth volumes of said frequency stabilizer, said flipflop connected to said control valve.

7. A respirator according to claim 6, wherein said control means further includes a pair of double diaphragm valves, each connected to a respective one of said third and fourth volumes, a volume valve connected between said respiration line and each of said double diaphragm valves for supplying gas through said double diaphragm valves to said respective third and fourth volumes to regulate a filling time of said third and fourth volumes.

8. A respirator according to claim 7, wherein each of said double diaphragm valves includes a housing, a pair of spaced diaphragms mounted in said housing and defining a central chamber, a central chamber of one of said double diaphragm valves connected to said third volume and a central chamber of the other of said double diaphragm valves connected to said fourth volume, said flipflop having two control lines connected to said control valve, each of said double diaphragm valve housings defining a pair of control spaces on sides of said diaphragms facing away from said central chamber of each double diaphragm valve, one of said control lines of said flipflop connected to one control space of each double diaphragm valve and the other of said control lines connected to the other control space of each of said double diaphragm valves.

9. A respirator according to claim 8, including a double diaphragm pressure ratio regulator connected to said respiration line between said control valve and a portion of said respiration line adapted for connection to a patient.

* * * * *